(12) United States Patent
Amirkhanian (10) Patent No.: US 8,617,374 B2
(45) Date of Patent: Dec. 31, 2013

(54) CAPILLARY ELECTROPHORESIS USING CLEAR COATED CAPILLARY TUBES

(75) Inventor: Varouj Amirkhanian, La Crescenta, CA (US)

(73) Assignee: Qiagen Sciences, LLC, Germantown, MD (US)

( * ) Notice: Subject to any disclaimer, the term of this patent is extended or adjusted under 35 U.S.C. 154(b) by 565 days.

(21) Appl. No.: 12/532,813

(22) PCT Filed: Mar. 26, 2008

(86) PCT No.: PCT/US2008/004031
§ 371 (c)(1),
(2), (4) Date: Sep. 23, 2009

(87) PCT Pub. No.: WO2008/118488
PCT Pub. Date: Oct. 2, 2008

(65) Prior Publication Data
US 2010/0108513 A1 May 6, 2010

Related U.S. Application Data

(60) Provisional application No. 60/919,984, filed on Mar. 26, 2007.

(51) Int. Cl.
*G01N 27/447* (2006.01)
(52) U.S. Cl.
USPC .................................. 204/603; 428/34.1
(58) Field of Classification Search
USPC ................ 204/452, 601, 603, 451; 428/34.1
See application file for complete search history.

(56) References Cited

U.S. PATENT DOCUMENTS

| | | | |
|---|---|---|---|
| 6,054,032 A * | 4/2000 | Haddad et al. | 204/451 |
| 6,661,510 B1 | 12/2003 | Hanning et al. | |
| 2005/0016852 A1 * | 1/2005 | Amirkhanian et al. | 204/600 |
| 2007/0014950 A1 * | 1/2007 | Stephen | 428/34.7 |

FOREIGN PATENT DOCUMENTS

| | | |
|---|---|---|
| EP | 1211325 | 6/2002 |
| JP | 2005-024361 | 1/2005 |
| WO | 03/001200 | 1/2003 |
| WO | 03/062815 | 7/2003 |
| WO | 2004/092721 | 10/2004 |
| WO | 2005/064325 | 7/2005 |
| WO | 2008-118488 | 10/2008 |

OTHER PUBLICATIONS

Bayer, www.bayercoatings.de (Urethane acrylate for high-performance coatings).*
Macomber, Joe, "UV Transparent Fluoropolymer Coated Capillary Tubing", LC-GC North America, vol. 24, Jun. 2006, p. 59.
PCT International Search Report of Counterpart PCT Application No. PCT/US2008/004031.

* cited by examiner

*Primary Examiner* — J. Christopher Ball
(74) *Attorney, Agent, or Firm* — Liu & Liu (57) ABSTRACT

A capillary tube having a hard, optically clear external coating or cladding. In one embodiment, the external clear coating comprises hard-fluoropolymer. The hard-fluoropolymer coating bonds to the fused silica glass, providing higher strength and superior static fatigue performance resulting in vastly improved bending flexibility. The thin hard-fluoropolymer coating of capillaries provides higher initial tensile strength, longer lifetime (resistance to stress corrosion or static fatigue) and superior ability to transmit excitation light and emitted light directly through the coating for fluorescence based detection.

19 Claims, 8 Drawing Sheets

CAPILLARY ELECTROPHORESIS USING CLEAR COATED CAPILLARY TUBES

This application claims the priority of U.S. Provisional Patent Application No. 60/919,984 filed on Mar. 26, 2007. This Provisional Patent Application is fully incorporated by reference herein, as if fully set forth herein. All other applications, patents, documents and references identified in the disclosure herein below, are fully incorporated by reference as if fully set forth herein.

BACKGROUND OF THE INVENTION

1. Field of the Invention

The present invention relates to capillary electrophoresis, and particularly an improved capillary tube for use to conduct capillary electrophoresis analysis.

2. Description of Related Art

Synthetic fused silica capillary tubing is widely used in the separation sciences, including the popular fields of Gas Chromatography, Capillary Liquid Chromatography, and Capillary Electrophoresis (CE). From its advent in the late 1970's, steady advances in product quality have emerged. Light guiding fused silica capillary tubing by applying soft fluoropolymer coating is the latest step in this continuing development. [See, Macomber Joe, Nelson Gary *Light Guiding Fused Silica Capillary Tubing*, As printed in LCGC, The APPLICATION NOTEBOOK—June 2002, Page 48.] Improved purity of the synthetic fused silica, more durable external coatings, and tightening of specification tolerances are cornerstones in capillary tubing advancements. Researchers have successfully used capillary tubing filled with a high refractive index liquid to form an optical wave-guide. In one specific application, a low refractive index, external soft fluoropolymer coated capillary was employed in a Raman spectroscopy device. [See, D. Che and S Liu, Long Capillary Waveguide Raman Cell, U.S. Pat. No. 5,604,587, 1997.] Although a viable product for light guiding applications, soft fluoropolymer coated capillary has never achieved the low cost or durability desired for the large volume disposable multi-channel capillary gel cartridges of the capillary electrophoresis type instrument.

High-performance capillary electrophoresis (HPCE) now represents a set of powerful electromigration techniques whose impact has been felt in virtually all areas of biochemical analysis. [See, Novotny, M. V.; Sudor, J. *Electrophoresis* 1993, 14, 373-389; Novotny, M. V. *High Performance Capillary Electrophoresis, Theory Techniques and Applications*, John Wiley & Sons: New York, 1998, Chapter 21, pp 729-765; Novotny, M. V. *Methods Enzymol.* 1996, 270, 101-133; Stefansson, M., Novotny, M. V. *Techniques In Glycobiology*, Marcel Dekker, New York, 1997, Chapter 26, pp 409-430.] HPCE is a micro fluidic approach to gel electrophoresis, whose greatest advantage is its diverse range of applications. CE technology with fluorescence based detection is commonly accepted by the biotechnology industry as a reliable, high resolution and highly sensitive detection tool. [See, Guttman, A. and Cook, N. *Anal. Chem.* 1991 63, 203 8-2042.]

The existing commercial CE systems with laser-induced fluorescence (LIF) detection mechanism that use multiple capillaries/channels for high-throughput applications are complicated in design and operation of the instrument. These systems utilize fused silica capillaries with polyimide coated jacket and a clear window area (i.e., with polyimide jacket removed at the window area) at the detection zone. Soft fluoropolymer coated capillaries have not been used in such multi-channel applications. The polyimide coating (jacket) provides strength and prevents the small OD glass capillaries from breakage. For fluorescence based detection, the polyimide jacket at the detection zone of the capillary must be removed. It is essential that the detection zone of the capillary tube to be completely free of any polyimide material or particulates to provide a clear optical path through the fused silica glass for excitation and direct emission detection/collection of fluorescence signal from the samples (bio-molecules) that are migrating or flowing inside the ID of the tubes.

To remove the polyimide jacket to provide a clear optical widow at the detection zone of the capillary for fluorescence detection, the polyimide jacket could be burned off by applying heat (using hot electric coils), acid etching, mechanical type scraping or removal (e.g., using a razor blade), or the jacket could be removed by photo-etching or photo-ablation techniques using different wavelengths and/or types of lasers. This process is very labor intensive and requires a careful examination of the glass surface under high magnification after the removal process to make sure the window (glass surface) is completely free of the polyimide jacket or any other particulates. Polyimide also fluoresces under visible light, which introduces further complications in the detection path. The removal of the polyimide jacket at the detection zone (e.g., a 3-5 mm long section) also poses weak joint exposing the bare capillary for possible micro-cracks or complete breakage. Excessive heat or mechanical stresses applied at the detection zone during the removal of the coated materials/jacket also produces micro-cracks in the OD and ID of the fused silica tube, which are not visible or detectable under the high power magnification, which also can increase the background fluorescence affecting the overall Limit of Detection (LOD) in CE type instruments, such as DNA fragment analysis type CE instruments.

SUMMARY OF THE INVENTION

The present invention overcomes the drawbacks of polyimide coated capillaries for CE. The present invention provides a low cost, optically effective capillary tube having high structural integrity.

One aspect of the present invention is directed to a hard coated, transparent or optically clear jacketed capillary tube. In one embodiment, the transparent or clear coated capillary tube comprises an external transparent or clear coating or cladding of hard-fluoropolymer. The hard-fluoropolymer coating bonds to the fused silica glass, providing higher strength and superior static fatigue performance resulting in vastly improved bending flexibility. The thin hard-fluoropolymer coating of capillaries provides higher initial tensile strength, longer lifetime (resistance to stress corrosion or static fatigue) and superior ability to transmit excitation light and emitted light directly through the jacket for fluorescence based detection. The hard polymer coated capillary is low in intrinsic fluorescence, which provides low background scattering and performs at least the same in signal-to-noise for DNA fragment gel capillary electrophoresis type applications, compared to prior art bare glass type capillaries with polyimide jacket removed. By using clear coated capillaries, there is no window burning required, which provides cost savings (less manual labor) and provides superior capillary strength within the detection zone for a reliable gel-cartridge assembly of electrophoresis type instruments. Since the detection zone (window) of the capillary tube is completely covered with the hard-fluoropolymer coated jacket, it also allows close fiber optic coupling (i.e., contacting the capillary exterior surface with greater optical coupling efficiency) to deliver excitation light or collect emission light from the separated samples at the center bore of the capillary, without cracking or breaking of the fragile glass capillary tubes. Another advantage is that one can cut the capillary tubes by diamond cleaving of the capillary tubes directly over the thin polymer coating, which provides clean cut glass surfaces without any carry over of the jacket at the distal (cut) ends. This further improves the manufacturing yield, which further reduces the overall assembly cost.

Another aspect of the present invention is directed to a CE system and a method of conducting CE using the inventive clear coated capillary tubes.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

DETAILED DESCRIPTION OF ILLUSTRATED EMBODIMENTS

This invention is described below in reference to various embodiments with reference to the figures. While this invention is described in terms of the best mode for achieving this invention's objectives, it will be appreciated by those skilled in the art that variations may be accomplished in view of these teachings without deviating from the spirit or scope of the invention.

The present invention provides a low cost, optically effective capillary tube having high structural integrity, for use in capillary electrophoresis systems.

Overview of CE System

Capillary electrophoresis (CE) generally is a micro fluidic approach to electrophoresis (micro-channel device to simplify gel electrophoresis). Its greatest advantage is its diverse range of applications. CE technology is commonly accepted by the biotechnology industry specifically in the DNA or nucleic acid-based testing as a reliable, high resolution and highly sensitive detection tool. CE with laser-induced fluorescence (LIF) is also one of the most powerful analytical tools for rapid, high-sensitivity and high-resolution bio-analysis/testing (e.g., DNA, carbohydrates, etc).

Figure 1:
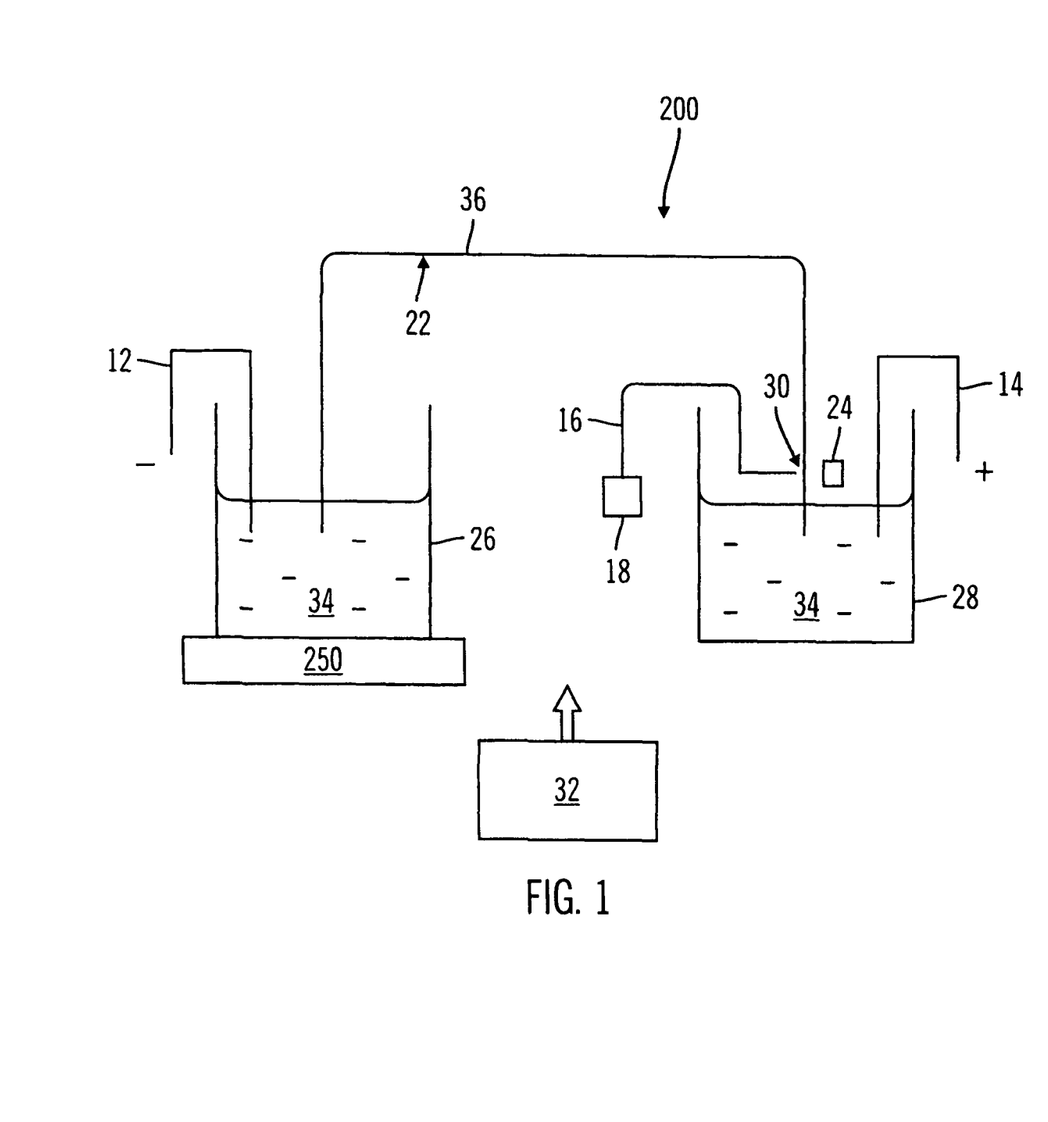
FIG. 1 is a schematic representation view of a capillary electrophoresis system in accordance with one embodiment of the present invention.

FIG. 1 is a schematic representation of a capillary electrophoresis (CE) system 200 in accordance with one embodiment of the present invention. The CE system 200 generally comprises a capillary separation column 22 (e.g., 200-500 μm O.D.), which defines a separation channel 36 (e.g., 5-200 μm I.D.). In accordance with the present invention, the capillary column 22 is made of fused silica (which is optically transparent), with a clear exterior coating (which is also optically transparent), as will be further disclosed below. The inside walls of the separation column 22 (i.e., the walls of the separation channel 36) may be coated with a material that can build up an electrostatic charge to facilitate electrophoresis and/or electrokinetic migration of the sample components. The separation channel 36 is filled with a separation support medium, which may be a running buffer or a sieving gel buffer specifically formulated for the particular biological sample under the prescribed operating and analysis conditions (e.g., for DNA, RNA, protein or carbohydrate type samples).

One end of the capillary column 22 is submerged in a reservoir 28 of running buffer/gel 34. The other end of the capillary column 22 is coupled to the sample vial 26. It is understood that other detection configurations implemented in a system similar to the CE system 200. A radiation detector 24 is positioned outside a transparent section of the capillary walls at detection zone 30. Given the transparent external hard coating of the capillary column 22 in accordance with the present invention, the entire longitudinal wall of the capillary column 22 would be available for locating the detection zone 30 as desired for the particular sample test. An excitation fiber 16 extends from a radiation source 18 (e.g., LED or laser) and is directed at the detection zone 30 outside the walls of the column. It is noted that the hard clear coating of the capillary column 22 is strong enough to provide structural support to the fused silica capillary tube body at the detection zone 30, such that no external sleeve or support would be necessary to provide structural integrity to this section of the capillary column 22. This is desirable because at the detection zone, there would not be interference with optical signals. Electrodes 12 and 14, that are part of the cartridge assembly are coupled to the buffer reservoirs 26 and gel reservoir 28 to complete the electrophoresis path.

Overview of CE Separation and Analysis

In operation, a prepared biological sample (e.g., a DNA or carbohydrate sample) in the sample vial 26 with a tagged fluorophore (i.e Ethidium Bromide or APTS) is introduced into the far end of the capillary column 22 away from the detection zone 30 by any of a number of ways (e.g., electrokinetic injection from the sample reservoir).

When a DC potential (e.g., 1-30 KV) is applied between electrodes 12 and 14, the sample components migrate under the applied electric potential along the separation channel 36 (e.g. DNA molecules that are negatively charged travels through the sieving gel toward a positive electrode as shown in FIG. 1) and separate into bands of sample components (e.g., DNA fragments). The extent of separation and distance moved along the separation channel 36 depends on a number of factors, such as migration mobility of the sample components, the mass and size or length of the sample components, and the separation support medium. The driving forces in the separation channel 36 for the separation of samples could be electrophoretic, pressure, or electro-osmotic flow (EOF) means.

When the sample reaches the detection zone, excitation radiation is directed via the excitation fiber 16 at the detection zone. The sample components fluoresce with intensities proportional to the concentrations of the respective sample components (proportional to the amount of fluorescent tag material). The detector 24 detects the intensities of the emitted fluorescence at a wavelength different from that of the incident radiation. The detected emitted radiation may be analyzed by known methods. For the automated system, a controller 32 (discussed below in connection with FIG. 5) on the electronic board 64 (FIG. 4) controls the operations of the CE system 200.

Capillary Cartridge

In accordance with one aspect of the present invention, the capillary column 22 described above having an external clear coating for electrophoresis may be a part of a removable cartridge that can be separated from the system for storage, transport or reuse. Different cartridges may be pre-assembled with different capillary properties (e.g., capillary size, internal coating and length), content, for example, a different gel-chemistry, with the content of the cartridge identified. Visual indicators may be provided to identify the cartridge and its contents. For example, a label (e.g., with a bar-code) or separate information sheet may be applied to the cartridge. In addition, in view of the reusability of the cartridge and defined usage or shelf life of the contents of the cartridge, a separate log may be associated with the particular cartridge for keeping track of the usage of the cartridge. A reusable capillary cartridge for use with a CE instrument could include a mechanism to automatically track information associated with a particular cartridge. The cartridge tracking data key feature is more fully described in copending patent application Ser. No. 11/022,313, which is fully incorporated by reference herein.

Figure 2:
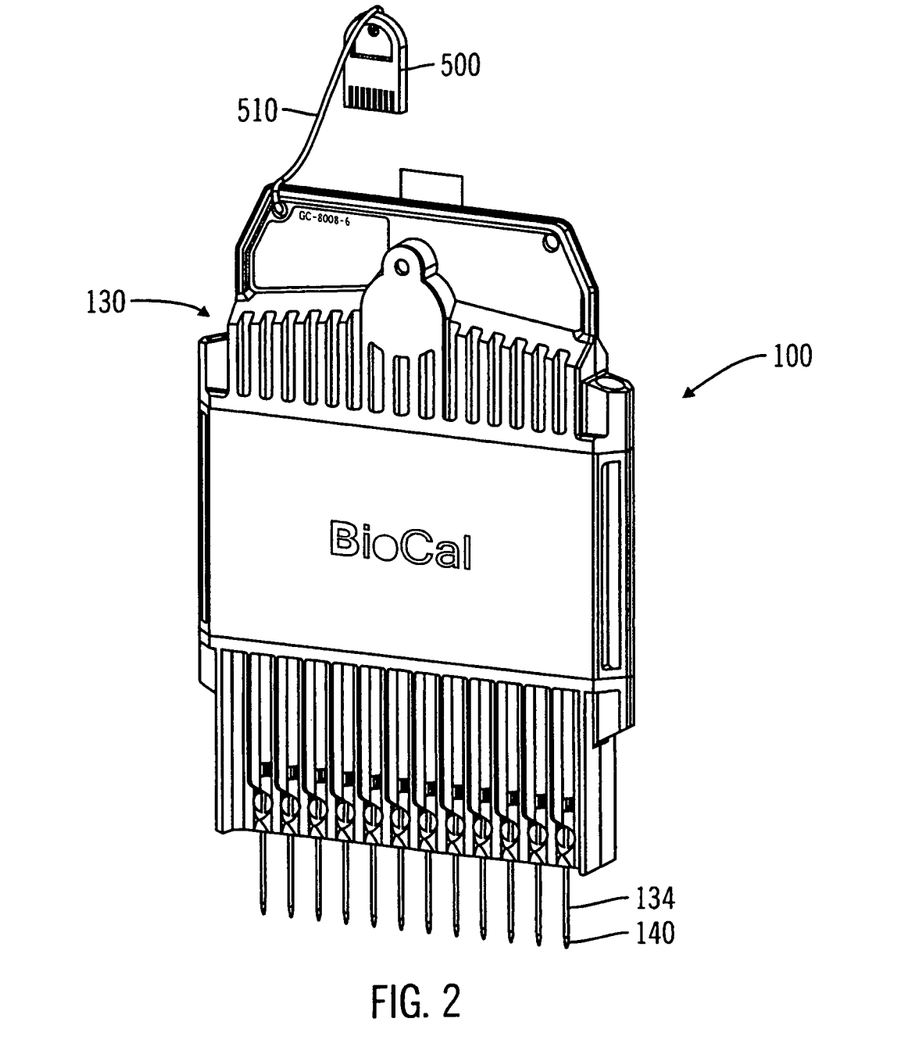
FIG. 2 is a perspective view of a capillary cartridge having a tracking device in accordance with one embodiment of the present invention.

FIG. 2 is a perspective view of the CE cartridge having a tracking data key in accordance with one embodiment of the present invention. The multi-channel capillary cartridge 200 includes twelve detection zones (schematically represented as 30 in FIG. 1), defined by capillaries 140 held in a cartridge body, which capillaries are similar to capillary columns 22 discussed above. A data key 500 is associated with the cartridge 100 (e.g., by a tether or cord 510 as shown). Details relating to the data key 500 is disclosed in copending application Ser. No. 11/022,313. The cartridge 100 includes a twelve-channel fused silica capillary array that is used for separation and detection of the samples as part of a disposable and/or portable, interchangeable cartridge assembly 100. The cartridge 100 shown in FIG. 2 holds up to 12 capillaries 140, 12-18 cm long. The cartridge 100 is integrated with a top, outlet buffer reservoir 130 common to all capillaries 140, which, when the cartridge 100 is installed in the CE system shown in FIGS. 3 and 4 (discussed below) is directly coupled by the interface mechanism 300 to a modular compressed gas source 78, such as a replaceable pressurized gas cartridge of an inert, compatible or non-reactive gas (e.g., Nitrogen, compressed air, $CO_2$, etc.) or a pressure pump. Appropriate pressure plumbing, including tubing, pressure valve and solenoid controls, is provided. (Details of such plumbing are omitted, since it is well within one skilled in the art to configure such plumbing given the disclosure herein of the functions, features and operations of the system 200.) The pressure source 78 provides the required gas pressure to fill-up all the 12-capillaries with the sieving gel contained in the reservoir 130 and to purge the gel from the previous run from the capillaries during the refilling process. Depending on the viscosity of the gel, pressures of up to 40 PSI may be applied to the capillaries 140 through the gel-filled reservoir 130.

Figure 6:
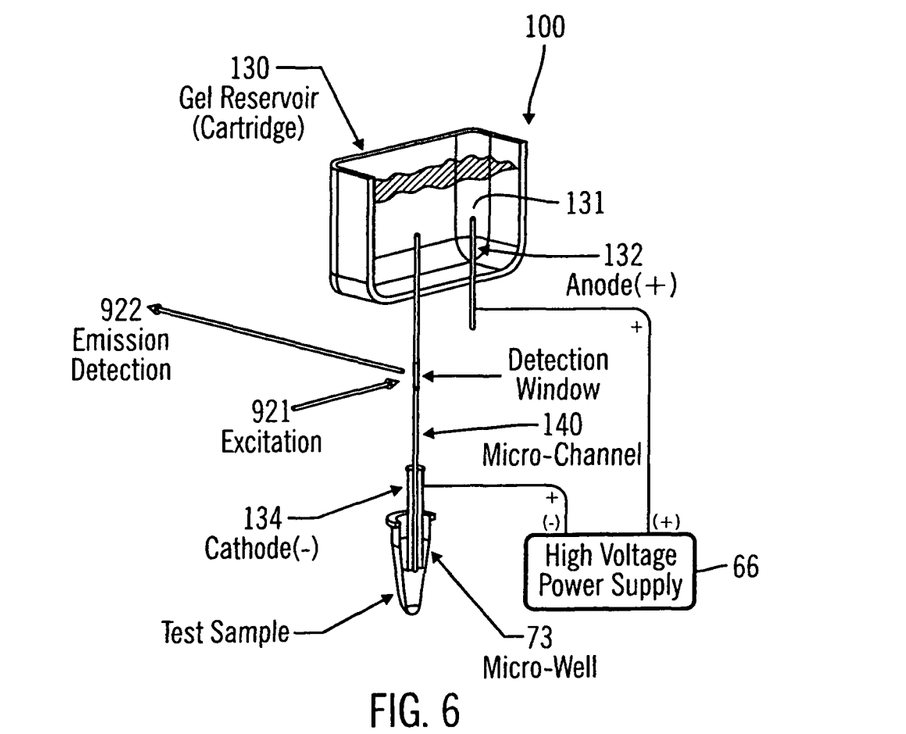
FIG. 6 is a schematic view of the capillary cartridge in relation to detection system and applied power in accordance with one embodiment of the present invention.

Referring to FIG. 6, the gel-cartridge 100 includes an integrated reservoir 130 containing a separation support medium (e.g., a gel matrix buffer) 131, which is common to all capillaries 140. The chemistry of the medium 131 and the characteristics of the capillaries 140 (e.g., capillary size, coating and length) are defined for each cartridge 100. The disposable gel-cartridges 100 can be packaged with small bore I.D. capillaries (i.e. 10-100 μm ID, 12-30 cm long) combined with low current (i.e., at low resistivity) and low viscosity type formulated linear polymer gel-matrix to provide high speed (shorter separation time) and higher resolution separations of sample (e.g., carbohydrate or DNA) fragments. The smaller bore capillaries (12-capillary cartridge) combined with the special formulated separation buffer/gel-matrix can achieve 250 or more continuous runs with a total current of <120 μA (typically 10-20 μA) without any damage to the gel matrix or loss of overall separation resolution.

The cartridge gel-reservoir 130 is equipped with a built in common electrode anode 132 (equivalent to anode 14 in FIG. 1) for all 12-capillaries 140, and each depending end of the capillaries 140 is provided with an external coaxial cathode 134. The anode 132 and cathodes 134 are automatically connected by the interface mechanism 300 to the high voltage power supply 76 (FIG. 4) for electrophoresis when installed inside the system 200. A fan or Peltier cooler (not shown) on the adjacent structure to the cartridge 100 may be provided to provide temperature control of the cartridge. In addition or in the alternate, the cartridge may have vent holes (input and output) for air circulation (temperature controlled air to be introduced to the cartridge from the instrument side). Depending on the heat generated during CE separation, the cartridge may simply be exposed to ambient temperature, with no auxiliary cooling features.

Figure 3:
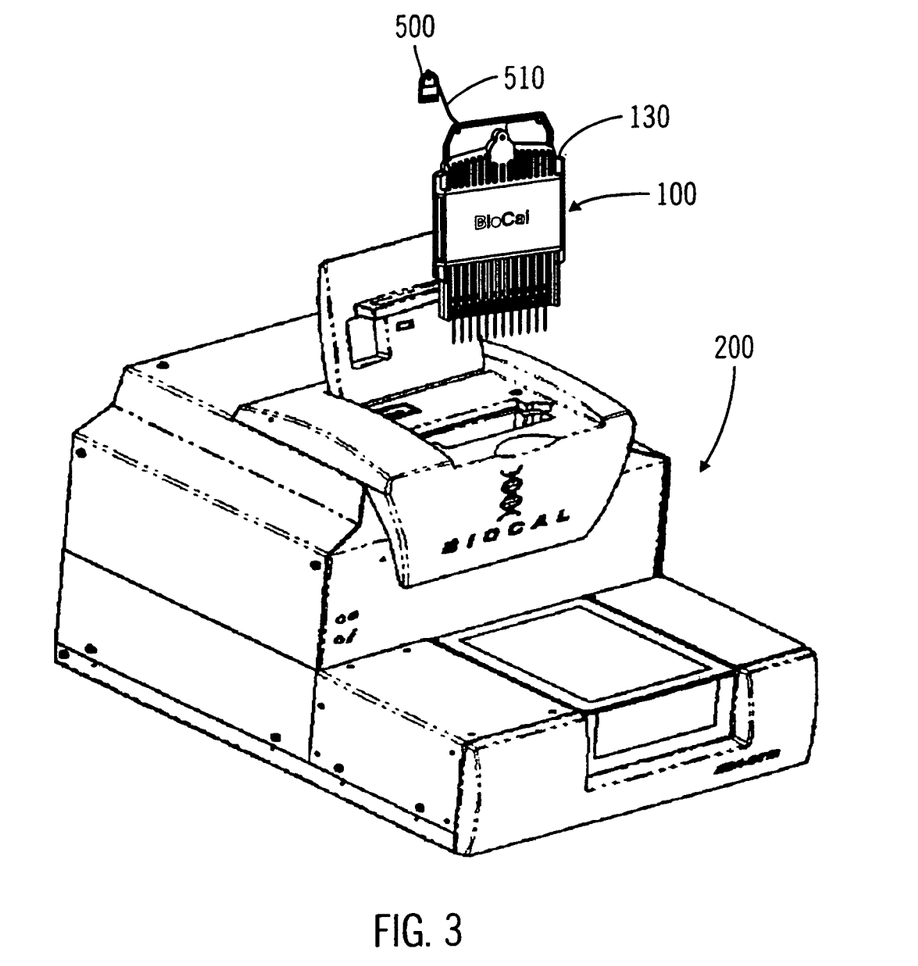
FIG. 3 is a perspective external view of a bio-analysis instrument that uses the capillary cartridge of FIG. 2, in accordance with one embodiment of the present invention.
Figure 4:
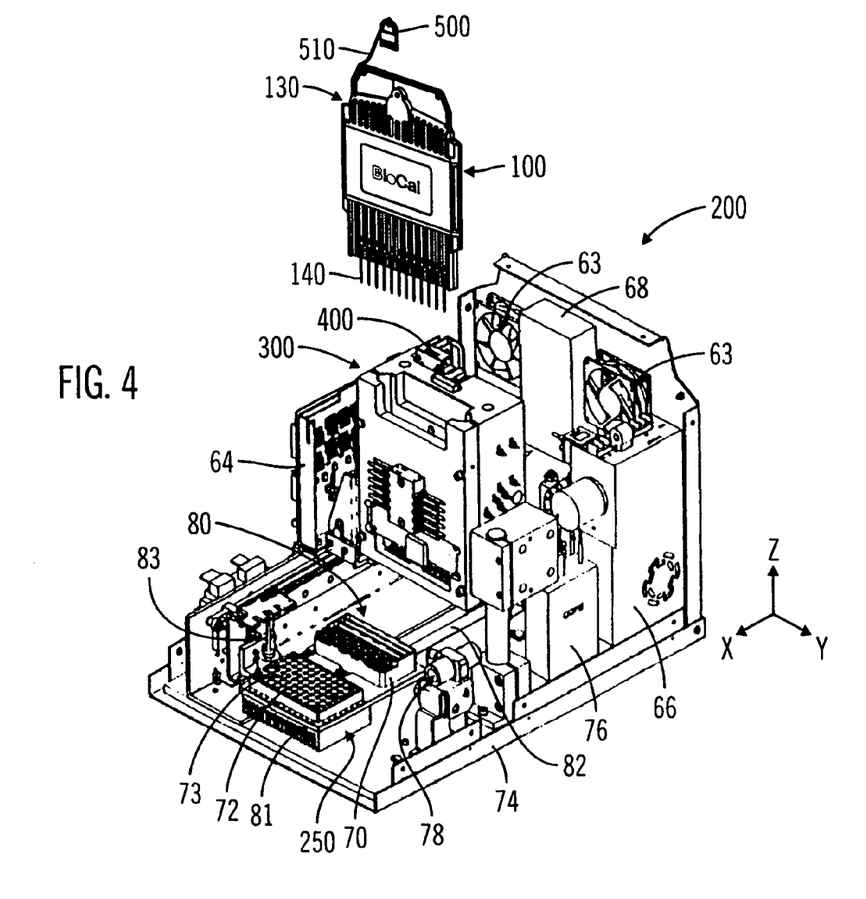
FIG. 4 is a perspective internal view of the bio-analysis instrument of FIG. 3, in accordance with one embodiment of the present invention.

In one embodiment, the cartridge 100 is received in the automated CE system 200 shown in FIGS. 3 and 4. A power supply 66 (FIG. 4) provides DC power to the CE system 200 to be supplied to the cartridge, as will be further explained below.

Further details of the cartridge may be referenced to the copending application Ser. No. 10/059,993, which is fully incorporated by reference herein.

Different cartridges can be easily interchanged in the bio-separation system to suit the particular sample based separation. The short and narrow bore capillaries combined with special sieving gel provides low operating current (<200 μA) at high applied voltages (e.g., 10 KV) without the need to cool the capillaries to achieve high speed, high resolution and high performance separations/results for large volume and low cost screening of bio-molecules such as DNA, carbohydrates, etc.

Clear Coated Capillary Tubes

Figure 8:
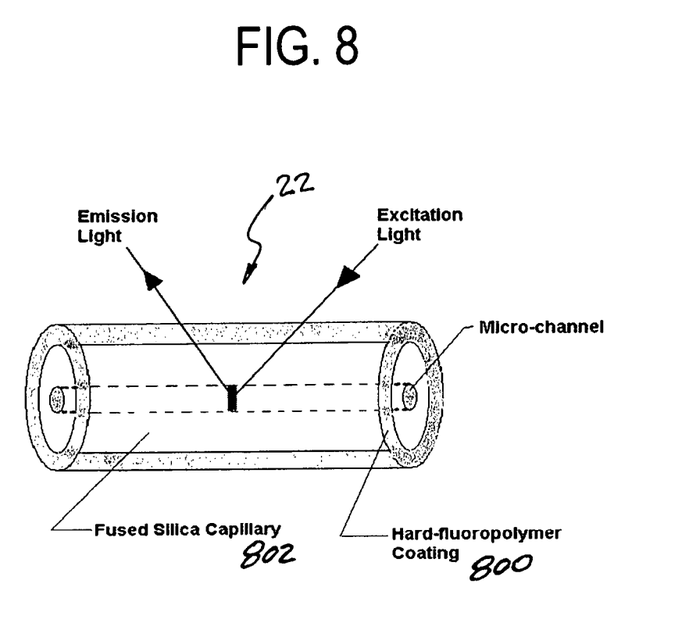
FIG. 8 illustrates a section of a capillary tube having a clear, hard-fluoropolymer coating, in accordance with one embodiment of the present invention.

One aspect of the present invention is directed a hard coated, transparent or optically clear jacketed capillary column or tube, which could be used in the gel-cartridge 100 discussed above. Referring to FIG. 8, in one embodiment, the clear coated capillary column 22 comprises a clear hard-fluoropolymer coating or cladding 800 on a fused silica capillary tube 802. A commercial embodiment of a clear coated capillary tube is available from InnovaQuartz Inc. in Phoenix Ariz.—TEQS™ Clad Silica Capillary, P/N:HOSBX075/363 (having an internal diameter of 75 μm and an overall outer diameter of 363 μm; coated capillaries with other dimensions are also available).

The composition of the hard fluoropolymer coating is itself not new to the inventors of the present invention. An example of a suitable fluoropolymer material has been developed by 3M Company (Minnesota Mining and Manufacturing Company) in reference to "TECS" (which stands for Technology Enhanced Clad Silica), which has been well documented in the optic fiber trade for coating or cladding optic fibers. References may also be made to the following U.S. Pat. Nos.: 4,654,235; 5,002,359; 5,690,863; 5,461,692; 7,317,857; and U.S. Patent Publication: 2005/0254765. The hard fluoropolymer coating may be directly applied to the fused silica capillary body without an intermediate buffer layer. The process of coating or cladding of bare capillary tubes with the same hard fluoropolymer coating is similar to the process of coating or cladding optic fibers with the same fluoropolymer.

In one embodiment, the clear silica cladding compositions are prepared from a 100% reactive composition of monofunctional and multi-functional monomers. The components of these compositions may be low molecular weight polymers of fluorine-containing monofunctional acrylate or methacrylate monomer(s), such polymers being soluble and dissolved in a fluorocarbon acrylate or methacrylate monomer or monomers, but not necessarily those of the base polymer. The cladding compositions may be prepared with or without a cross-linking monomer such as a di-functional or poly-functional acrylate of methacrylate. The claddings may also use a thermal or photoinitiator or other known polymerization initiating system and an adhesion promoter or promoters, such as acrylic or methacrylic acid, a silanol acrylate, methacrylate, alkoxysilane acrylate or methacrylate, or an alkoxy vinyl silane, aryl acrylate or methacrylate.

The clear coated capillary may have 200-500 μm O.D., and a 5-200 μm I.D. The clear coating may have a 5-50 μm thickness.

The hard-fluoropolymer coating bonds to the fused silica glass, providing higher strength and superior static fatigue performance resulting in vastly improved bending flexibility. The thin hard-fluoropolymer coating of capillaries provides higher initial tensile strength, longer lifetime (resistance to stress corrosion or static fatigue) and superior ability to transmit excitation visible light directly through the coating and emitted light directly through the coating for fluorescence based detection, as shown in FIG. 8. The hard polymer coated capillary is low in intrinsic fluorescence, which provides low background scattering and performs at least the same in signal-to-noise for DNA fragment gel capillary electrophoresis type applications, compared to prior art bare glass type capillaries with polyimide jacket removed. By using clear coated capillaries, there is no window burning required, which provides cost savings (less manual labor) and provides superior capillary strength within the detection zone for a reliable gel-cartridge assembly of electrophoresis type instruments. Since the detection zone (window) of the capillary tube is completely covered with the hard-fluoropolymer coated jacket, it also allows close fiber optic coupling (i.e., contacting the capillary exterior surface with greater optical coupling efficiency) to deliver excitation light or collect emission light from the separated samples at the center bore of the capillary, without cracking or breaking of the fragile glass capillary tubes. Another advantage is that one can cut the capillary tubes by diamond cleaving or laser cleaving/cutting of the capillary tubes directly over the thin polymer coating, which provides clean cut glass surfaces without any carry over of the jacket at the distal (cut) ends. This further improves the manufacturing yield, which further reduces the overall assembly cost. Simplifying the cutting/cleaving process of the glass capillaries with the clear polymer coating, provides simplicity in optical detection system design of the new instrument, which reduces the manufacturing cost, while improving the reliability and reproducibility.

The external clear fluoropolymer coating may cover the entire length of the capillary tube, or cover only a longitudinal section of the capillary tube to define the detection zone. At least the detection zone of the capillary tube should be covered by the clear coating, to define a clear window for excitation light and emission light through the clear coating for light induced fluorescence detection. It is noted that with the entire length of the capillary tube externally coated with the hard clear coating, the detection zone may be defined anywhere as appropriate for the particular CE experiment. Compared to the prior art polyimide coated capillaries, the detection zone does not need to be defined by removing the polyimide coating at a particular section of the capillaries. Further, with the hard external clear coating, no external sleeve or other support is required to protect the capillary tube from breakage or other damage. The hard clear coating provides sufficient structural support to the capillary tube at the detection zone, so that no external support would be required at the detection zone. Accordingly, there would be no external structure that could interfere with the optical detection components and optical signals (e.g., optic fibers for excitation and/or detection).

Multiple Capillary Cartridge Based CE System

BioCal Technology, Inc. (which is wholly owned by eGene, Inc.), the assignee of the present invention, developed a CE-based automated instrument (e.g., Model HDA-GT12 Analyzer System). The illustrated embodiment of the automated instrument is based on BioCal's CE instrument, which incorporates low-cost and sensitive optical detection technology, integrated reagent cartridge and micro-fluidic electrophoresis principle for a real-time fluorescent analysis, to form a sensitive and accurate bioanalysis detection system. The system is designed to be high-throughput, easy-to-use, portable, inexpensive, very robust and for field operation/applications. The cartridge developed by BioCal is designed to be supported by the instrument, with all essential cartridge elements aligned and coupled to support elements in the instrument. The cartridge is held with respect to sample trays that can be moved in relation to the capillary separation channels in the cartridge.

FIG. 4 shows an overall perspective view of the internal components of the CE system 200 (e.g., a carbohydrate or DNA analyzer). FIG. 3 is an external view of the system. The CE system 200 incorporates an interface mechanism 300, in accordance with one embodiment of the present invention. The interface mechanism 300 supports a multi-channel cartridge 100 in accordance with the one embodiment of the present invention, which provides easy handling of multi-channel separation columns, and allows easy optical coupling of the detection zones to the detection optics of the CE system 200.

The fully automated CE system 200 has a base 74, supporting a modular X-Z mechanism 80 having a sample tray support frame 81. The X-Z mechanism 80 supports and moves a buffer plate 70 in relation to the multi-capillary cartridge 100 supported by the interface mechanism 300, and a sample holder (e.g., a 96-well micro-titer plate 72) which may be held in an optional sample preparation device 250. Specifically, the mechanism 80 comprises an X mechanism 82 for moving the support frame 81 along the X-direction relative to the cartridge 100, and a Z mechanism 83 for moving the sample & buffer tray in the Z direction relative to the support frame 81 and the cartridge 100. The sample preparation device 250, if provided, may be controlled by a thermoelectric controller 68 (see FIG. 5).

Figure 7:
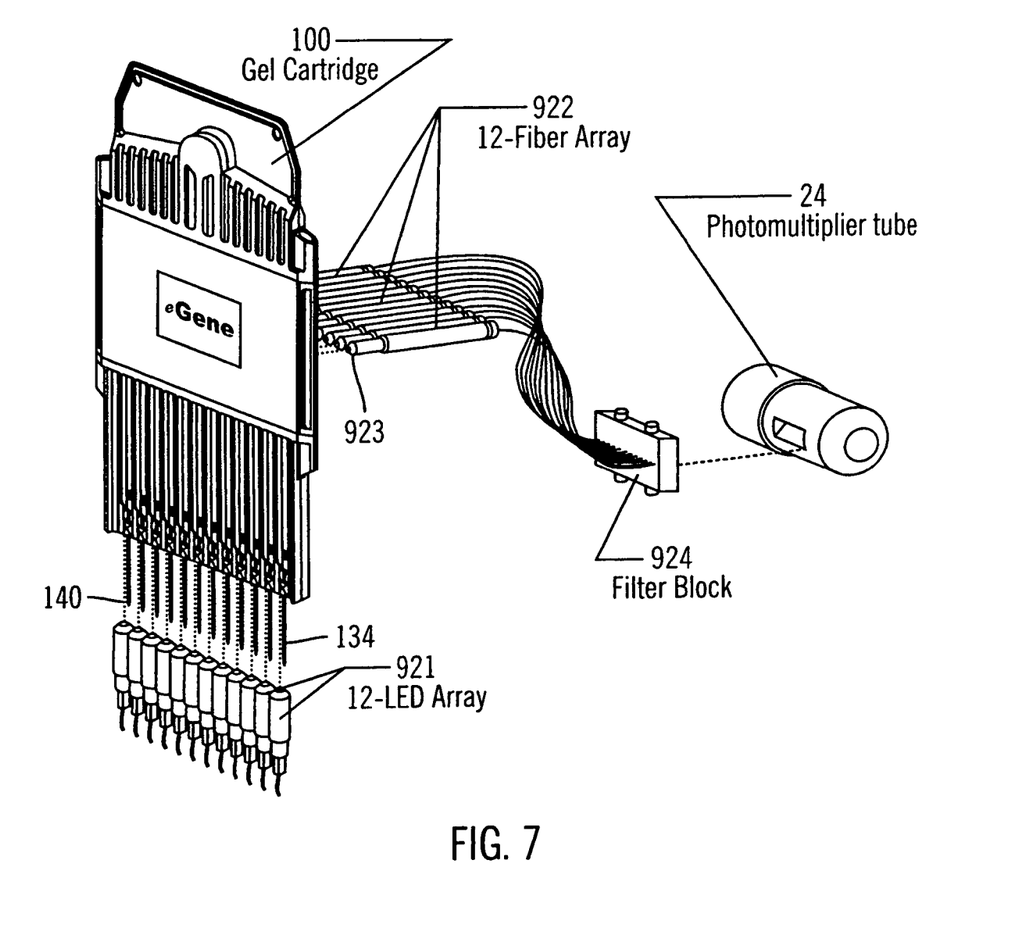
FIG. 7 is a partial perspective view of the capillary cartridge in relation to detection system in accordance with one embodiment of the present invention.

Referring also to FIGS. 6 and 7, twelve excitation LEDs 921 are time-multiplexed (with a sampling frequency of 10-100 Hz), producing multiplexed signals to the 12 separation micro-channels (capillary tubes 140) and proportionally twelve time-staggered emitted fluorescence signals (FIG. 7) are then collected by 12-micro-ball lenses 923 and are coupled to twelve emission detection optical fibers (12-fiber array) 922, which are relayed down to a single photomultiplier tube (PMT detector) 24 via a filter block 924. The gel-cartridge 100 supports 12 fused silica capillaries 140 for CE separation (FIGS. 6 and 7).

Other structures and operations of the interface mechanism 300 of the CE system 200 may be referenced to the copending U.S. patent application Ser. No. 10/823,382, which is fully incorporated by reference herein. The cartridge interface accomplishes quick and reliable interface connections to the disposable gel contained capillary cartridge 100. These interface connections include a gas pressurization connection (not shown in FIG. 7), high voltage connections (anode 132 and cathodes 134), and precision optical connections. The interface also provides precise and repeatable mechanical positioning of the cartridge, to accurately position the components of the cartridge in relation to the support elements in the CE system 200, including positioning the capillary tips in relation to external sample or buffer reservoirs, found on 96-well titer plate, for example. Additionally, given the interface provides separate electrical, optical and pneumatic connections to each separation channel, there would be channel-to-channel isolation from cross talk both electrically and optically and insulation to the rest of the instrument from high voltage.

Detection System

U.S. Pat. Nos. 6,828,567 and 6,870,165 are fully incorporated by reference herein, which more specifically disclose the time staggered/multiplexed detection scheme that can be adopted in the CE system 200.

In one embodiment, for radiation induced visible fluorescence detection, the excitation radiation would in the range of 400-700 nm, with emitted radiation induced from the excitation radiation generally in a similar range. (For example, excitation wavelength range would be from 400-600 nm (centered at 500 nm) and emission detection range would be 500-700 nm (centered at 600 nm)). The excitation light sources 921 (FIG. 7) could be super-bright LEDs (i.e. Agilent's InGaN LEDs in colors of blue, green, etc.), or other inexpensive, compact, low-power light sources for use in the detection scheme of the present invention. These super-bright LEDs based on InGaN material technology (HLMP-CB15 and HLMP-CM15 from Agilent) have an average light output power of 2.5-3 mW. The spectral characteristics of these blue-green InGaN LEDs with their Peak Wavelengths of 470 and 530 nm and halfwidths (nm) of 30 to 50 nm are good candidates to be used for excitation of dyes (e.g. fluorescin, rhodamine, Etidium Bromide, thiazol orange), with excitation spectra in the range of 450 to 550 nm. Any solid state light source that can be pulsed could also be used with any dye or fluorophor for this type of time-multiplexed detection. Since the response time of these LEDs are very high (few hundred nanoseconds in frequency ranges of 1 Hz-to-100 MHz), they could be pulsed at greater forward currents (e.g., 15-30 mA, but could be up to 100 mA forward current in pulsed mode operation), to obtain high radiant peaks. Pulsed operation of LEDs can typically be achieved by the transistor drive circuits. Significantly higher peak LED light output can be realized from large drive current pulses at lower duty cycles than DC operation. Another example is LED-array module consisting of Green 524 mn LEDs, which can also be adopted as excitation light sources for the fluorescence detection of a low-cost CE instrument. Laser diodes in the range of 400-900 nm, and more specifically in the range of 400-600 nm may also be used, for example.

The filter block 927 (FIG. 7) can be a 500-700 nm (or more specifically, 570-630 nm) long pass optical filter (OG-590).

Control of the Automated System 200

The CE system 200 provides an integrated controller to operate the various components of the system. The operations of the CE system 200, including the interface mechanism 300 with the I/O port 400, detection system, power supply, X-Y control system, etc., are controlled by a controller 32 interfacing with an external user control interface (e.g., a PC 918), to coordinate the functions described herein.

Figure 5:
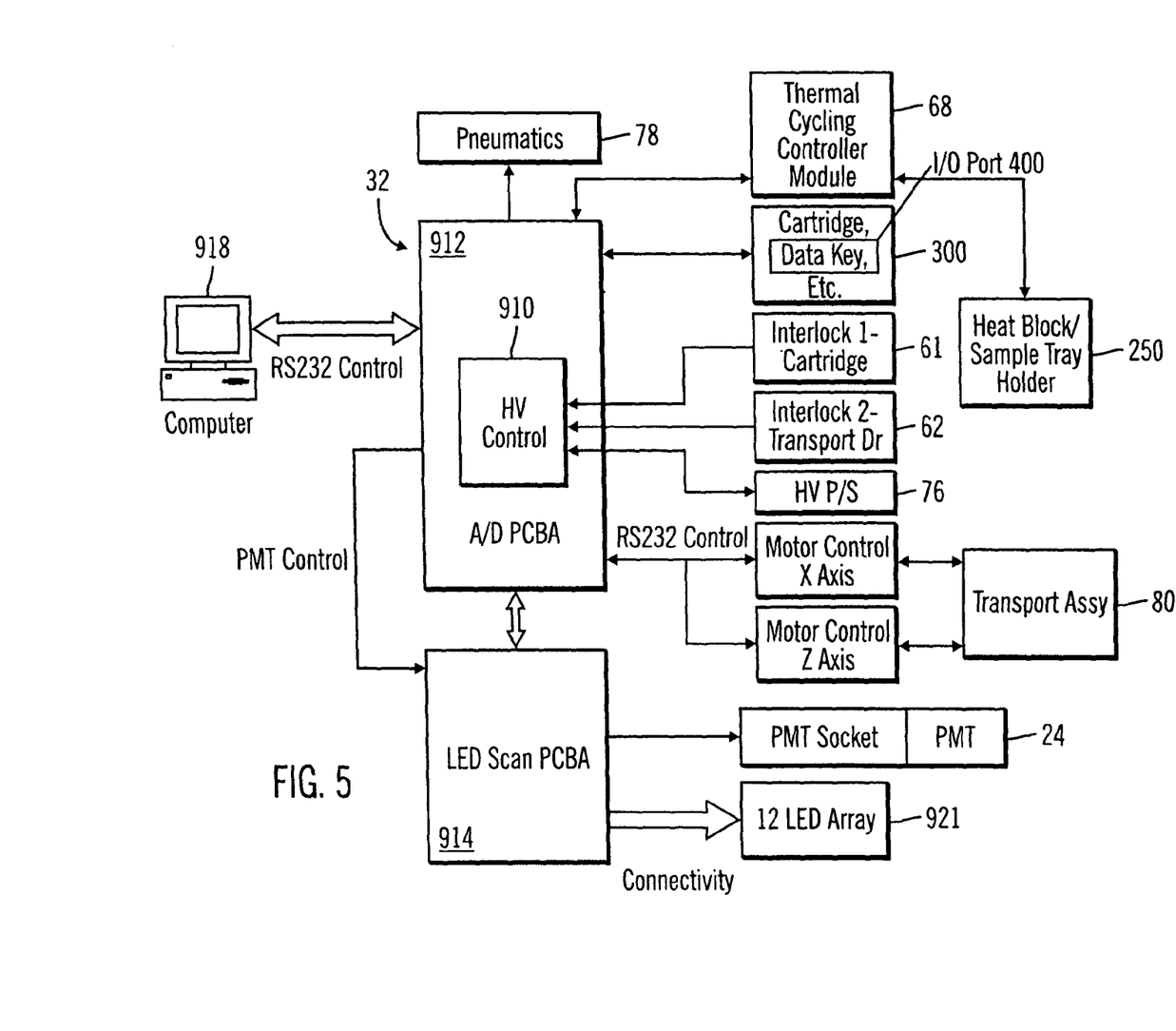
FIG. 5 is a block diagram of the control system for the bio-analysis instrument in accordance with one embodiment of the present invention.

Referring also to FIG. 5, in accordance with one embodiment of the present invention, the block diagram of the controller 32 for the CE system 200 is illustrated. The controller 32 comprises a processor as part of the A/D Board (LED Processor PCBA) 912 with CPU 910 for converting detection signals received from the detector 24 (e.g., a PMT) to corresponding digital signals, coming from LEDScan PCBA interface 914 for transferring and receiving signals to and from respective parts of the CE system 200 by instructions from the CPU 910. The A/D (LED Processor PCBA) interface 912 is coupled to the various actuators and the I/O port 400 in the interface mechanism 300 to control and connect (using the interface mechanism 300) at least high voltage power supply 76, pneumatics 78 (hidden from view in the interface mechanism 300 in FIG. 2), motor controls (X-Z sample/buffer tray) 80 and interlocks (cartridge and transport doors) 61 and 62 (details of these are not shown in the interface mechanism 300 in FIG. 2). The A/D or LED Processor PCBA 912 also controls the high-voltage power supply 76 for sample injection and electrophoresis functions of the CE system 200, a circuit 914 (LEDScan Board) for modulating the excitation radiation source (e.g., LEDs) 921 and the detector module 24 of the CE system 200. Details of the modulation of the excitation radiation source may be referenced to copending U.S. patent application Ser. No. 10/060,052, which had been fully incorporated by reference herein.

The A/D (LED Processor PCBA) 912 may be further coupled to an external personal computer 918, which in turn performs data processing or additional control function for the CE system 200, e.g., using BioCal's BioCalculator Software to control various features and functions of the automated multi-channel CE system 200.

The components of the controller 32, with the exception of the PC 918, may be packaged as an electronic board 64 (FIG. 4) and cooling fans 63, on board the CE system 200 and electrically coupled to the PC 918 via a serial port (not shown), or they may be part of a separate controller module outside of the CE system 200. The CPU 910 and/or the PC 918 are programmed to accomplish the various control functions and features for the CE system 200. In one embodiment, the PC 918 can be configured to provide the user control interface for the CE system 200 (e.g., user initiation of the connection sequence of the interface mechanism 300). It would be within a person skilled in the art to implement the program code given the functions and features disclosed herein. In an alternate embodiment, the controller 32 or components thereof may be incorporated as part of the PC 918.

Operation of CE System

Once the capillary cartridge 100 and the data key 500 have been mated to the instrument, the cartridge ID and the number of pre-programmed runs available from the cartridge 100 are read by the CE system 200 via the I/O port 400. The CE system 200 may employ an algorithm to determine if the capillary cartridge 100 has enough runs left to complete the process cycle before initiating the CE sequence. Otherwise, the CE system 200 may display an error message and the sequence is stopped. If it is determined that the capillary cartridge 100 has sufficient runs available, the CE sequence will start and number of runs is tracked by the CE system. At the end of the analysis, the number of remaining runs is calculated and sent to the data key 500 for storage.

The controller 32 of the instrument may be configured to "authenticate" the cartridge 100 and conduct an integrity check to determine if the particular cartridge 100 has the correct properties (e.g., gel-chemistry, number of channels/capillaries) for the particular sample analysis to be conducted. The instrument may also confirm that the user falls within the class of users permitted to use the particular cartridge. Further, the instrument may communicate/record information concerning usage of the cartridge 100 (e.g., usage history, sequence/method steps/parameter settings, patient I.D., test parameters, and perhaps test results). Such information provides an update to the stored information from the previous use of the cartridge. Further reading and writing can be controlled with respect to the data and information discussed above relating to the data key 500. The instrument may go through other checks to authenticate the test protocols the user wants to apply to the particular cartridge is proper, to determine if there are any limitations, restrictions or constraints, such as those noted before.

In operation of the CE analysis, the sample handling tray transport mechanism 80, with a 96-well plate (8×12) 72 and buffer tray 70, is used to introduce the samples (or analytes) to each capillary 140. The X-Z transport mechanism 80 indexes a row of sample carrying wells 73 in the micro-titer plate 72 under the row of capillary tips 140 and dip the tips into the well. By applying a voltage, electrokinetic injection moves a known amount of the analytes to the beginning of the separation column 140. After injection, the analytes from sample tray 72 may be replaced with a running buffer from tray 70. Alternatively, after injection, the transport mechanism 80 may index to move a row of 12 wells of the titer plate 72 into position under the capillaries 140 of the cartridge 100 to replace the twelve wells containing the analytes.

By applying high voltage across the total length of the capillary 140, separation of the analytes is achieved. As the fragments approach the end of the capillaries 140 and enter into the detection zone, the excitation light energy (e.g., from twelve LEDs delivered by optical fibers) is directed at the detection zone, illuminating the migrating fragments. The detection scheme may be in a time-staggered manner as disclosed in U.S. Pat. Nos. 6,828,567 and 6,870,165, which have been incorporated by reference herein.

To prepare for the next run with a different sample, the old gel from the previous run is purged from the capillaries by pressuring the reservoir to refill the capillaries with fresh gel. The trays 70 carry cleaning solutions, waste collection, and samples. The purged gel is collected by one of the trays 70 by positioning the tips of the capillaries at a row of waste collecting wells in one of the trays. The tips of the capillaries may be cleaned with water or a cleaning solution by positioning and dipping the tips of the capillaries in such solution in the appropriate tray wells. When the capillaries are refilled and ready for the next run, the tips of the capillary are dipped into the samples by repositioning the tray 72. The above mentioned sequence of process may be programmed as one of the automated functions of the controller 32. The interface mechanism 300 provides the interfacing of support elements in the CE system 200 to the cartridge, such as high voltage, gas pressure, LED radiation source, and detection optics, as described above.

After the analysis has been completed, the cartridge 100 may be retrieved and reused when needed for another analysis at a later time or date. If a different run condition is contemplated, a different cartridge having different attributes and properties may be used instead. The data key mechanism of the present invention would automatically keep track of the usage of the different interchangeable cartridges, without requiring the user to manually keep track of such.

While the invention has been particularly shown and described with reference to the preferred embodiments, it will be understood by those skilled in the art that various changes in form and detail may be made without departing from the spirit, scope, and teaching of the invention.

For example, interface mechanisms may be adapted to receive capillary cartridges of other structural designs. By way of example and not limitation, the detection scheme of the present invention is described in connection with capillary electrophoresis and radiation induced fluorescence detection. It is understood that the present invention is also applicable to detection of radiation emissions other than fluorescence emissions, including other types of emissive radiation, such as phosphorescence, luminescence and chemiluminescence, as well as UV and visible absorbance based detection. Furthermore, while the separation channels in the described embodiments are defined by cylindrical columns or tubes, it is understood that the concepts of the present invention is equally applicable to columns or tubes of various cross-sections (such as square, rectangular or essentially semicircular cross sections).

Accordingly, the disclosed invention is to be considered merely as illustrative and limited in scope only as specified in the appended claims.

I claim:

1. A capillary tube, comprising:
a longitudinal transparent tubular body defining a bore; and
a clear transparent hard coating on the body, allowing light to transmit between the bore and external of the transparent hard coating through the hard coating, wherein the transparent hard coating comprises a clear hard-coated polymer, wherein the hard-coated polymer comprises a fluoropolymer material.

2. A cartridge for bio-analysis, comprising:
a body;
at least one capillary tube as in claim 1 supported by the body;
a reservoir in fluid communication with the capillary tube; and
a separation matrix formulated for electrophoretic analysis contained in the reservoir.

3. The cartridge as in claim 2, wherein there is a plurality of capillary tubes supported by the body of the cartridge, each covered by the transparent coating, and wherein the reservoir is common to the plurality of capillary tubes.

4. A bio-analysis system, comprising:
a base;
a cartridge as in claim 2;
a cartridge interface support on the base, interfacing with the cartridge; and
a controller operatively coupled to the cartridge interface to control operations of the cartridge interface.

5. The bio-analysis system as in claim 4, further comprising a detection system optically coupled to a detection zone of each capillary tube, wherein the detection system includes at least excitation radiation directed at the detection zone or detection of emitted radiation from the detection zone.

6. The bio-analysis system as in claim 5, wherein the detection system comprises radiation induced fluorescence detection.

7. The bio-analysis system as in claim 6, wherein the excitation and emitted radiations are generally in the range of 400-700 nm.

8. A method for bioanalytical analysis, comprising:
providing a cartridge as in claim 2;
introducing a sample into one end of each capillary tube;
undertaking electrophoresis separation along each capillary tube, to separate the sample into components; and
analyzing the separated components.

9. The method as in claim 8, wherein the separated components are analyzed using a detection system optically coupled to a detection zone of each capillary tube, wherein the detection system includes at least excitation radiation directed at the detection zone or detection of emitted radiation from the detection zone.

10. The method in claim 9, wherein the detection system comprises radiation induced fluorescence detection.

11. The method as in claim 10, wherein the excitation and emitted radiations are generally in the range of 400-700 nm.

12. The capillary tube as in claim 1, wherein a sample flows through the bore of the tubular body, and wherein emitted light from the sample transmits from the bore through the hard coating to external of the hard coating.

13. The capillary tube as in claim 12, wherein the hard coating and the tubular body have close optical coupling to transmit emitted light from the bore through the tubular body and the hard coating.

14. The cartridge as in claim 2, wherein a sample flows through the bore of the tubular body, and wherein emitted light from the sample transmits from the bore through the hard coating to external of the hard coating.

15. The cartridge as in claim 14, wherein the hard coating and the tubular body have close optical coupling to transmit emitted light from the bore through the tubular body and the hard coating.

16. The bio-analysis system as in claim 5, wherein a sample flows through the bore of the tubular body of the capillary tube, wherein the detection system is optically coupled to the detection zone from outside of the hard coating, and wherein emitted radiation from the sample transmits from the bore through the hard coating to the detection system outside of the hard coating.

17. The bio-analysis system as in claim 16, wherein the hard coating and the tubular body have close optical coupling to transmit emitted light from the bore through the tubular body and the hard coating.

18. The method as in claim 9, wherein a sample flows through the bore of the tubular body of the capillary tube, wherein the detection system is optically coupled to the detection zone from outside of the hard coating, and wherein emitted radiation from the sample transmits from the bore through the hard coating to the detection system outside of the hard coating.

19. The method as in claim 18, wherein the hard coating and the tubular body have close optical coupling to transmit emitted light from the bore through the tubular body and the hard coating.

* * * * *